(12) United States Patent
Batchelder

(10) Patent No.: US 9,636,872 B2
(45) Date of Patent: May 2, 2017

(54) METHOD FOR PRINTING THREE-DIMENSIONAL PARTS WITH PART STRAIN ORIENTATION

(71) Applicant: Stratasys, Inc., Eden Prairie, MN (US)

(72) Inventor: J. Samuel Batchelder, Somers, NY (US)

(73) Assignee: Stratasys, Inc., Eden Prairie, MN (US)

( * ) Notice: Subject to any disclaimer, the term of this patent is extended or adjusted under 35 U.S.C. 154(b) by 547 days.

(21) Appl. No.: 14/202,608

(22) Filed: Mar. 10, 2014

(65) Prior Publication Data

US 2015/0251356 A1 Sep. 10, 2015

(51) Int. Cl.
| | | |
|---|---|---|
| *G05B 99/00* | (2006.01) | |
| *B29C 67/00* | (2017.01) | |
| *G01N 3/08* | (2006.01) | |
| *G05B 15/02* | (2006.01) | |
| *B33Y 50/02* | (2015.01) | |
| *G05B 19/4099* | (2006.01) | |
| *G06F 17/50* | (2006.01) | |
| *G01N 33/00* | (2006.01) | |

(52) U.S. Cl.
CPC .......... *B29C 67/0088* (2013.01); *B33Y 50/02* (2014.12); *G01N 3/08* (2013.01); *G05B 15/02* (2013.01); *G05B 19/4099* (2013.01); *G01N 2033/0078* (2013.01); *G05B 2219/49023* (2013.01); *G06F 17/50* (2013.01); *G06F 2217/12* (2013.01); *Y02P 90/265* (2015.11)

(58) Field of Classification Search
None
See application file for complete search history.

(56) References Cited

U.S. PATENT DOCUMENTS

| | | |
|---|---|---|
| 5,503,785 A | 4/1996 | Crump et al. |
| 5,764,521 A | 6/1998 | Batchelder et al. |
| 5,943,235 A | 8/1999 | Earl et al. |
| 6,004,124 A | 12/1999 | Swanson et al. |
| 6,021,358 A | 2/2000 | Sachs |
| 6,070,107 A | 5/2000 | Lombardi et al. |
| 6,099,573 A | 8/2000 | Xavier |
| 6,118,456 A | 9/2000 | Cooper |
| 6,228,923 B1 | 5/2001 | Lombardi et al. |

(Continued)

FOREIGN PATENT DOCUMENTS

| | | |
|---|---|---|
| EP | 1448359 B1 | 7/2007 |
| WO | 2009047355 A1 | 4/2009 |

OTHER PUBLICATIONS

Huang et al., "Sloping wall structure support generation for fused deposition modeling", the International Journal of Advanced Manufacturing Technology, 2009, pp. 1074-1081.

(Continued)

*Primary Examiner* — Isaac T Tecklu

(74) *Attorney, Agent, or Firm* — Westman, Champlin & Koehler, P.A.

(57) ABSTRACT

A method and program for printing a three-dimensional part with an additive manufacturing system, the method including generating or otherwise providing strain data from a digital model of the three-dimensional part, orienting the digital model to align the directions of high tensile strain in a build plane, and printing the three-dimensional part in a layer-by-layer manner based on the oriented digital model with the additive manufacturing system.

20 Claims, 10 Drawing Sheets

(56) References Cited

U.S. PATENT DOCUMENTS

| | | |
|---|---|---|
| 6,264,873 B1 | 7/2001 | Gigl et al. |
| 6,407,748 B1 | 6/2002 | Xavier |
| 6,408,321 B1 | 6/2002 | Platt |
| 6,450,393 B1 * | 9/2002 | Doumanidis ............ B23P 15/00 156/264 |
| 6,532,394 B1 | 3/2003 | Earl et al. |
| 6,682,684 B1 | 1/2004 | Jamalabad et al. |
| 6,790,403 B1 | 9/2004 | Priedeman et al. |
| 6,828,965 B2 | 12/2004 | Rockwood |
| 6,907,307 B2 | 6/2005 | Chen et al. |
| 6,923,634 B2 | 8/2005 | Swanson et al. |
| 7,084,870 B2 | 8/2006 | Fang et al. |
| 7,122,246 B2 | 10/2006 | Comb et al. |
| 7,228,519 B2 | 6/2007 | Aoki et al. |
| 7,305,367 B1 | 12/2007 | Hollis et al. |
| 7,308,328 B2 | 12/2007 | Fang et al. |
| 7,373,286 B2 | 5/2008 | Nikolskly et al. |
| 7,384,255 B2 | 6/2008 | LaBossiere et al. |
| 7,403,833 B2 * | 7/2008 | Heide ..................... G06F 17/50 700/119 |
| 7,428,481 B2 | 9/2008 | Nikolskly et al. |
| 7,500,846 B2 | 3/2009 | Eshed et al. |
| 7,590,462 B2 | 9/2009 | Rubbert et al. |
| 7,604,470 B2 | 10/2009 | LaBossiere et al. |
| 7,625,200 B2 | 12/2009 | Leavitt |
| 7,747,305 B2 | 6/2010 | Dean et al. |
| 7,773,087 B2 | 8/2010 | Fowler et al. |
| 7,810,025 B2 | 10/2010 | Blair et al. |
| 7,831,328 B2 * | 11/2010 | Schillen ................ B29C 67/007 264/401 |
| 7,840,393 B1 | 11/2010 | Whirley et al. |
| 7,848,838 B2 | 12/2010 | Gershenfeld et al. |
| 7,891,964 B2 | 2/2011 | Skubic et al. |
| 7,896,209 B2 | 3/2011 | Batchelder et al. |
| 8,032,337 B2 | 10/2011 | Deichmann et al. |
| 8,153,182 B2 | 4/2012 | Comb et al. |
| 8,219,234 B2 | 7/2012 | Kritchman et al. |
| 8,323,017 B2 | 12/2012 | Kritchman et al. |
| 8,419,996 B2 | 4/2013 | Swanson et al. |
| 2003/0227455 A1 | 12/2003 | Lake et al. |
| 2004/0006405 A1 | 1/2004 | Chen et al. |
| 2004/0095343 A1 | 5/2004 | Forest et al. |
| 2004/0217095 A1 * | 11/2004 | Herzog ................ B22F 3/1055 219/121.85 |
| 2005/0131570 A1 | 6/2005 | Jamalabad et al. |
| 2005/0140678 A1 | 6/2005 | Gielis et al. |
| 2006/0098009 A1 | 5/2006 | Zumiga |
| 2006/0111807 A1 | 5/2006 | Gothait et al. |
| 2006/0155418 A1 | 7/2006 | Bradbury et al. |
| 2008/0079731 A1 | 4/2008 | Shearer |
| 2008/0184185 A1 | 7/2008 | Sailzer et al. |
| 2008/0192044 A1 | 8/2008 | Fowler et al. |
| 2008/0192046 A1 | 8/2008 | Fowler et al. |
| 2008/0192051 A1 | 8/2008 | Fowler et al. |
| 2008/0261165 A1 | 10/2008 | Steingart et al. |
| 2009/0263582 A1 | 10/2009 | Batchelder |
| 2010/0096072 A1 | 4/2010 | Hopkins et al. |
| 2010/0096485 A1 | 4/2010 | Taatjes et al. |
| 2010/0096489 A1 | 4/2010 | Taatjes et al. |
| 2010/0190556 A1 | 7/2010 | Chan |
| 2010/0283172 A1 | 11/2010 | Swanson |
| 2010/0291505 A1 | 11/2010 | Rawley et al. |
| 2011/0076495 A1 | 3/2011 | Batchelder et al. |
| 2011/0076496 A1 | 3/2011 | Batchelder et al. |
| 2011/0178621 A1 | 7/2011 | Heide |
| 2012/0267827 A1 | 10/2012 | Kritchman et al. |
| 2013/0040091 A1 * | 2/2013 | Dikovsky ........... B29C 67/0059 428/68 |
| 2014/0178588 A1 | 6/2014 | Swanson et al. |
| 2015/0080495 A1 * | 3/2015 | Heikkila ............ B29C 67/0055 523/223 |
| 2015/0217367 A1 * | 8/2015 | Dickey ............... B29C 67/0088 164/133 |
| 2015/0331402 A1 * | 11/2015 | Lin ....................... G05B 15/02 700/119 |
| 2016/0096318 A1 * | 4/2016 | Bickel ................ B29C 67/0051 264/40.1 |
| 2016/0256925 A1 * | 9/2016 | Heikkila ................ B22F 1/004 |

OTHER PUBLICATIONS

Huang et al., "Slice Data Based Support Generation Algorithm for Fused Deposition Modeling", Tsinghua Science and Technology, Jun. 2009, vol. 14, pp. 223-228.

International Search Report and Written Opinion dated Dec. 21, 2012 for corresponding International Patent Application No. PCT/US2012/054421, filed Sep. 10, 2012.

* cited by examiner

METHOD FOR PRINTING THREE-DIMENSIONAL PARTS WITH PART STRAIN ORIENTATION

BACKGROUND

The present disclosure relates to methods and programs for printing three-dimensional (3D) parts with additive manufacturing systems. In particular, the present disclosure relates to methods and programs for printing 3D parts with orientations based on strain data, such as for increasing part strengths.

Additive manufacturing systems (e.g., 3D printers) are used to print or otherwise build 3D parts from digital representations of the 3D parts (e.g., AMF and STL format files) using one or more additive manufacturing techniques. Examples of commercially available additive manufacturing techniques include extrusion-based techniques, jetting, selective laser sintering, powder/binder jetting, electron-beam melting, and stereolithographic processes. For each of these techniques, the digital representation of the 3D part is initially sliced into multiple horizontal layers. For each sliced layer, a tool path is then generated, which provides instructions for the particular additive manufacturing system to print the given layer.

For example, in an extrusion-based additive manufacturing system, a 3D part may be printed from a digital representation of the 3D part in a layer-by-layer manner by extruding a flowable part material. The part material is extruded through an extrusion tip carried by a print head of the system, and is deposited as a sequence of roads on a substrate in an x-y plane. The extruded part material fuses to previously deposited part material, and solidifies upon a drop in temperature. The position of the print head relative to the substrate is then incremented along a z-axis (perpendicular to the x-y plane), and the process is then repeated to form a 3D part resembling the digital representation.

In fabricating 3D parts by depositing layers of a part material, supporting layers or structures are typically built underneath overhanging portions or in cavities of 3D parts under construction, which are not supported by the part material itself. A support structure may be built utilizing the same deposition techniques by which the part material is deposited. The host computer generates additional geometry acting as a support structure for the overhanging or free-space segments of the 3D part being formed. Support material is then deposited from a second nozzle pursuant to the generated geometry during the printing process. The support material adheres to the part material during fabrication, and is removable from the completed 3D part when the printing process is complete.

SUMMARY

The present disclosure is directed to a method and an associated program for printing a 3D part with an additive manufacturing system. The method includes generating or otherwise providing strain data from a digital model of the three-dimensional part (e.g., performing a finite element analysis on the digital model), and orienting the digital model to align directions of high tensile strain in a build plane. In some embodiments, the method may also include generating interior fill tool paths for one or more sliced layers of the digital model based on the strain data.

Preferably, the orienting of the digital model involves determining a dominant tensile strain direction (and, in some embodiments, a secondary tensile strain direction) from the strain data, and aligning each of the dominant tensile strain direction and the secondary tensile strain direction in the build plane. In some embodiments, the dominant and secondary tensile strain directions are respectively based on $\hat{x}_i$ directions (from diagonalized strain tensors) of the highest and second highest volume-averaged tensile strains $u_i$, and/or the highest and second highest weighted volume-averaged tensile strains $U_i^n$.

The method also includes printing the 3D part in a layer-by-layer manner based on the oriented digital model with the additive manufacturing system. Aligning the directions of highest tensile strain in the build plane preferably directs the highest strains primarily against the intralayer strengths of the 3D part, as opposed to the interlayer strengths of the 3D part.

In one aspect, the present disclosure is directed to a method for printing a 3D part with an additive manufacturing system, where the method includes providing a digital model of the 3D part to a computer-based system, generating strain data from the digital model with the computer-based system, determining a dominant tensile strain direction for the digital model from the strain data with the computer-based system, orienting the digital model to align the dominant tensile strain direction in a build plane of the additive manufacturing system, and printing the 3D part in a layer-by-layer manner with the additive manufacturing system based on the oriented digital model. In some embodiments, the method also includes determining a secondary tensile strain direction for the digital model from the strain data, where orienting the digital model also aligns the secondary tensile strain direction in the build plane of the additive manufacturing system.

In another aspect, the present disclosure is directed to a method for printing a 3D part with an additive manufacturing system, where the method includes performing a finite element analysis on a digital model with a computer-based system to produce a plurality of strain tensors, calculating volume-averaged tensile strains from the plurality of strain tensors with the computer-based system, and determining a dominant tensile strain direction and a secondary tensile strain direction for the digital model from the calculated volume-averaged tensile strains with the computer-based system. The method also includes orienting, with the computer-based system, the digital model to align each of the dominant tensile strain direction and the secondary tensile strain direction in a build plane of the additive manufacturing system, generating printing instructions based on the oriented digital model with the computer-based system, and printing the three-dimensional part in a layer-by-layer manner with the additive manufacturing system based on the generated printing instructions.

In a further aspect the present disclosure is directed to a program stored on a computer storage medium, and configured to be operated by a processor of a computer-based system to perform steps that include generating strain data for a digital model, determining a dominant tensile strain direction for the digital model from the generated strain data, and orienting the digital model to align the dominant tensile strain direction in a build plane of an additive manufacturing system associated with the program. In some embodiments, the performed steps also include determining a secondary tensile strain direction for the digital model from the strain data, where the performed step of orienting the digital model also aligns the secondary tensile strain direction in the build plane of the additive manufacturing system.

The performed steps also include generating printing instructions based on the oriented digital model, and transmitting the generated printing instructions from the computer-based system to the associated additive manufacturing system for printing a 3D part in a layer-by-layer manner with the additive manufacturing system based on the generated printing instructions.

DEFINITIONS

Unless otherwise specified, the following terms as used herein have the meanings provided below:

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present disclosure.

Directional orientations such as "above", "below", "top", "bottom", and the like are made with reference to a layer-printing direction of a 3D part. In the embodiments shown below, the layer-printing direction is the upward direction along the vertical z-axis. In these embodiments, the terms "above", "below", "top", "bottom", and the like are based on the vertical z-axis. However, in embodiments in which the layers of 3D parts are printed along a different axis, such as along a horizontal x-axis or y-axis, the terms "above", "below", "top", "bottom", and the like are relative to the given axis.

The term "build plane" refers to a plane in which the layers of a 3D part are arranged, and is perpendicular to the layer-printing direction of the 3D part.

The term "providing", such as for "providing a consumable material", when recited in the claims, is not intended to require any particular delivery or receipt of the provided item. Rather, the term "providing" is merely used to recite items that will be referred to in subsequent elements of the claim(s), for purposes of clarity and ease of readability.

The terms "first", "second", and the like, when recited in the claims with reference to an item of a plurality of items, is not intended to limit the item to any particular order of sequence or arrangement, and is merely used for ease of understanding and readability. For example, "a first sliced layer of a plurality of sliced layers" and "the plurality of sliced layers comprise a first sliced layer" are not limited to a bottom-most or top-most sliced layer of a digital model. Rather, they each merely refer to a sliced layer of the plurality of sliced layers.

The terms "about" and "substantially" are used herein with respect to measurable values and ranges due to expected variations known to those skilled in the art (e.g., limitations and variabilities in measurements).

DETAILED DESCRIPTION

The present disclosure is directed to a method and an associated computer-based program for printing 3D parts with orientations based on strain data, where the strain data is preferably attained by analyzing digital models associated with the 3D parts. A current goal in additive manufacturing is the ability to print 3D parts having bulk part strengths that match those attained with injection molding techniques. While additive manufacturing techniques are generally capable of achieving high intralayer part strengths (i.e., within the same layer, such as in an x-y build plane), the layer-by-layer nature of additive manufacturing limits the interlayer part strengths along the printing directions (e.g., z-directions). As such, the interlayer bonds of 3D parts can be points of failure when the 3D parts are subjected to high tensile stresses.

Figure 1A:
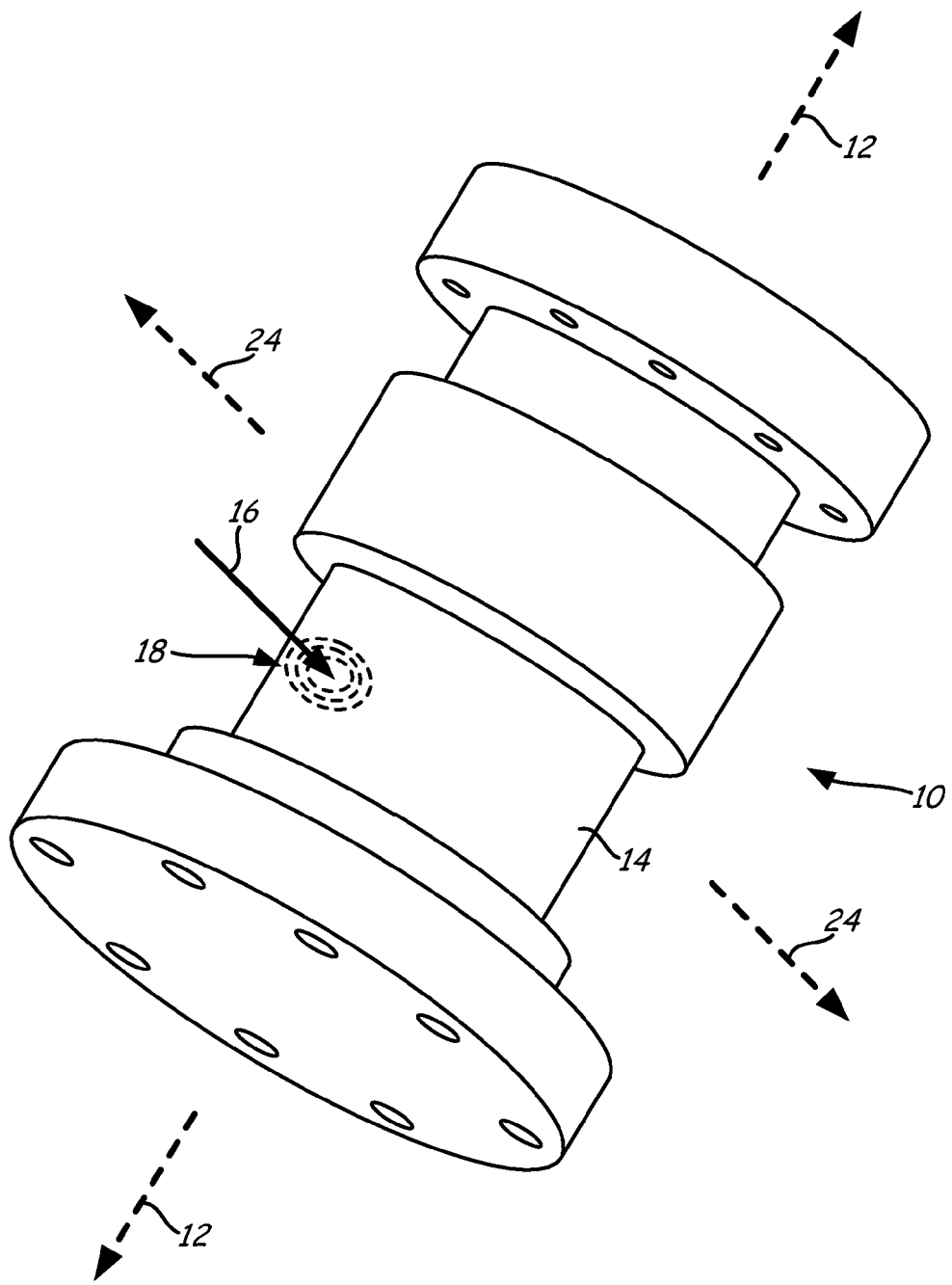
FIG. 1A is an illustration of a printed 3D part in an initial orientation in an x-y-z coordinate system.

This presents an issue as 3D parts become more and more popular for end uses as strong real parts, where they can be routinely subjected to high tensile stresses. Current part orientation techniques are primarily focused on reducing build times, reducing material consumptions (e.g., to minimize support material volumes), part packing techniques, and the like. While these are valuable techniques for many applications, orienting the digital models based on these criteria can undesirably position the printed 3D parts such that the locations of high strain are aligned with the weaker interlayer strengths. For example, if a user desires to print 3D part 10 shown in FIG. 1A with reduced support material volumes, 3D part 10 is preferably oriented such that the printing direction extends along axis 12 (as further shown below in FIG. 2A).

Figure 1B:
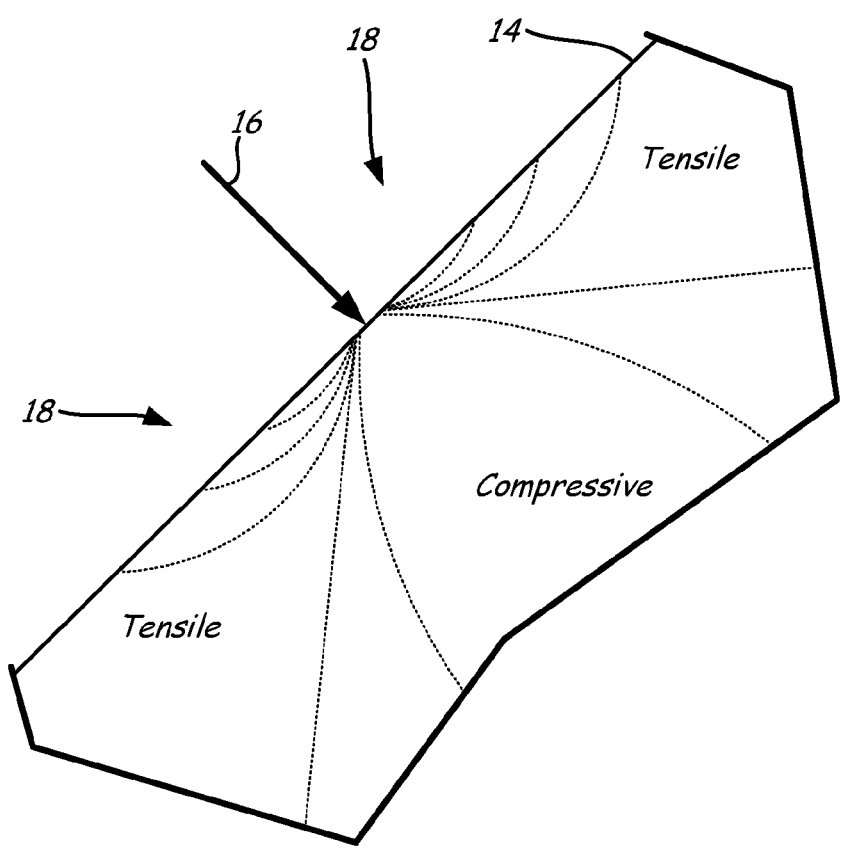
FIG. 1B is an expanded sectional view taken from FIG. 1A, illustrating compressive and tensile strains from an applied stress load.

However, if 3D part 10 is intended for use in a manner in which the sidewall 14 of 3D part 10 will be subjected to a high normal stress, such as illustrated by arrow 16, sidewall 14 will be strained under compression and tension due to the applied load, as illustrated by isostrain lines at region 18. This is further illustrated in FIG. 1B, showing a partial cross-section of 3D part 10 within sidewall 14. As shown, the strain on 3D part 10 extends from the Hertzian contact location of arrow 16 and sidewall 14, where the dashed lines illustrate regions of substantially constant strain.

The volume of 3D part 10 below the Hertzian contact location is subjected to compressive stresses. Since the compression is spatially localized, there is also a shallow region of strong tensile radial stresses adjacent to the contact edge, corresponding to the surface isostrain lines at region 18. The tensile radial stresses decrease quickly decrease when moving inward from sidewall 14, and eventually become the compressive stresses. However, these strong tensile radial stresses at region 18 can subject sidewall 14 to crack under the generated tensile strain.

Figure 2A:
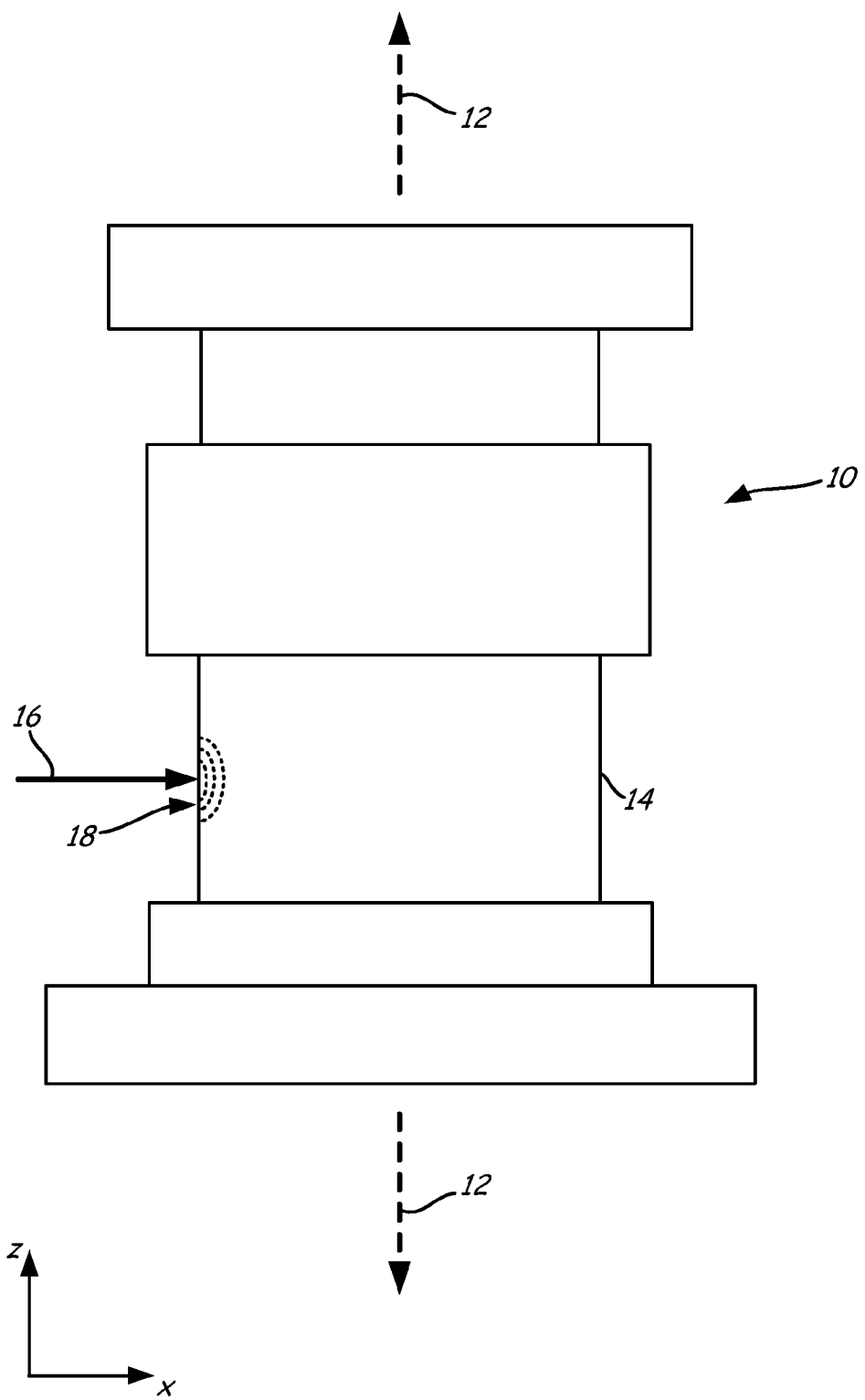
FIG. 2A is an illustration of the 3D part oriented in the x-y-z coordinate system to minimize support material volumes.
Figure 2B:
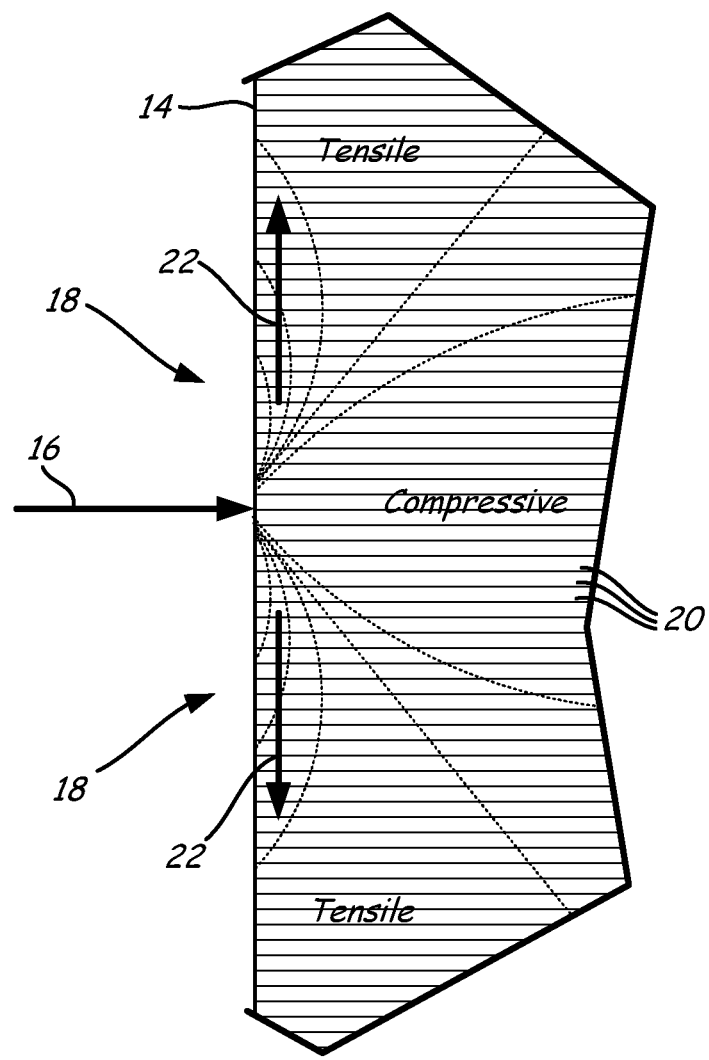
FIG. 2B is an expanded sectional view of layers of the 3D part oriented as shown in FIG. 2A, also illustrating compressive and tensile strains from the applied stress load.

As such, if 3D part 10 is oriented such that the printing direction is along axis 12, as illustrated in FIG. 2A, then the generated tensile strain at region 18 will be applied to the weaker interlayer bonds of 3D part 10. This is depicted in FIG. 2B, which is an expanded sectional view of region 18, illustrating layers 20 of 3D part 10 when oriented with a printing direction along axis 12.

As shown, the applied stress in the direction of arrow 16 generates tensile strains that are primarily directed at the bonds between layers 20 along the printing direction, as illustrated by arrows 22, and which are perpendicular to the x-y build plane. As mentioned above, the interlayer bonds between layers 20 are typically weaker than the intralayer bonds within each layer 20. As can be appreciated, this can potentially increase failure rates of 3D part 10 during its intended use, resulting in surface cracking at sidewall 14.

Figure 3A:
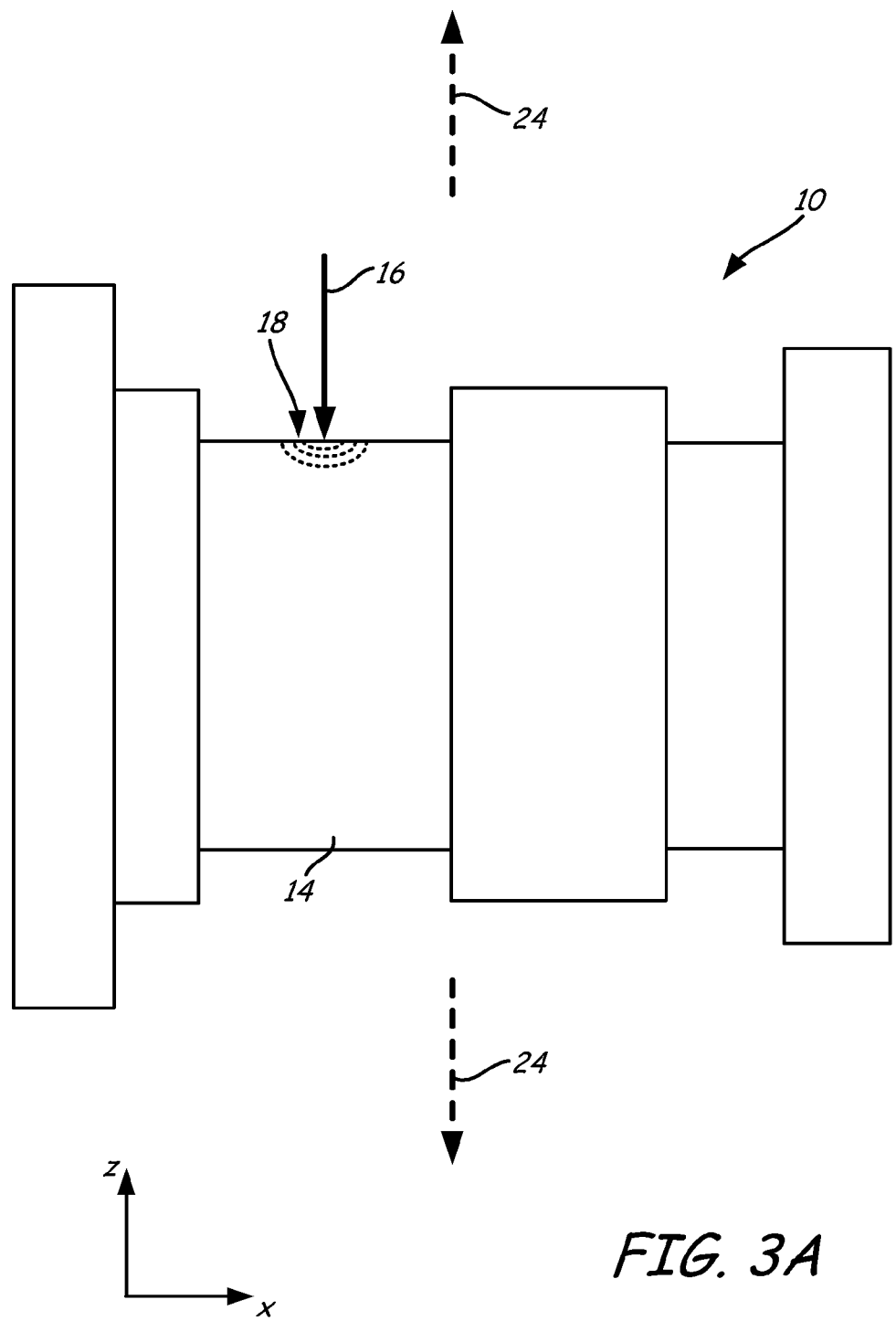
FIG. 3A is an illustration of the 3D part oriented in the x-y-z coordinate system to increase part strength pursuant to the method of the present disclosure.

Accordingly, the method of the present disclosure focuses on orienting a digital model such that the directions of high strain are aligned with the higher intralayer strength of the printed 3D part, namely in the build plane of the printed 3D part. For instance, as shown in FIG. 3A, 3D part 10 may be oriented such that high tensile strain in region 18 is aligned in the x-y build plane of 3D part 10. In this case, 3D part 10 is oriented such that the printing direction extends along axis 24.

Figure 3B:
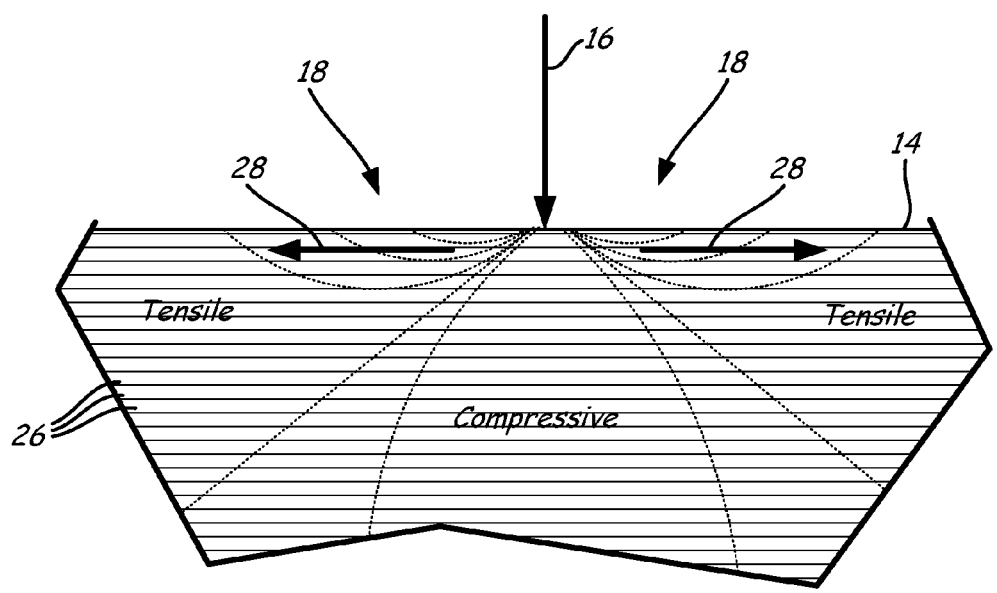
FIG. 3B is an expanded sectional view of layers of the 3D part oriented as shown in FIG. 3A, also illustrating compressive and tensile strains from the applied stress load.

This orientation directs the high tensile strains primarily against the higher intralayer strength of 3D part 10. This is depicted in FIG. 3B, which is an expanded sectional view of region 18 illustrating layers 26 of 3D part 10 when oriented with a printing direction along axis 24. As shown, the applied stress in the direction of arrow 16 generates tensile strains that are primarily directed at the bonds within layers 26, as illustrated by arrows 28, as opposed to the weaker interlayer bonds between layers 26.

While the orientation shown in FIGS. 3A and 3B may possibly increase the build time and amount of materials consumed (e.g., more support material required) compared to the orientation shown in FIGS. 2A and 2B, the orientation shown in FIGS. 3A and 3B effectively increases the strength of 3D part 10 for its intended use. In many applications, this increased part strength can vastly outweigh the longer build times and higher material consumptions.

The above discussion of the applied stress load along arrow 16 and the resulting strain at region 18 illustrates a simple example for ease of explanation. More typically, the strain profiles of 3D parts subjected to stress loads are highly complex, and in many situations, are counter intuitive. As such, as discussed below, the method of the present disclosure provides an efficient and hands-free technique for orienting 3D parts that can accommodate a variety of different strain profiles regardless of their complexities.

Briefly, the method involves analyzing a digital model of a 3D part (e.g., 3D part 10) to generate strain data for the 3D part, such as with a finite element analysis (FEA) program. It is understood that strain, stress, and deformation of a 3D part are related to each other. As such, while discussed herein as using "strain data" (e.g., strain tensors), the method of the present disclosure may also rely on stress data (e.g., stress tensors) and deformation data attained from the analysis program.

The resulting strain data for the digital model may then be used to orient the digital model in a coordinate system such that directions of high tensile strain are aligned in the x-y build plane, where they are directed at the higher intralayer strengths. The oriented digital model may then undergo slicing, support generation, tool path generation, and the like for printing the desired 3D part with an additive manufacturing system.

As also discussed below, in some embodiments, the road propagation direction of the interior fill tool paths of each sliced layer for the oriented 3D part may also be aligned with directions of high tensile strain. The intralayer strength of each layer 26 in 3D part 10 is typically greatest in its road propagation direction, as opposed to a direction that is perpendicular to the road propagation direction. This is reduced somewhat by orienting the road propagation of each adjacent layer 26 in a different direction (e.g., the serpentine raster fill directions are rotated by 30 degrees, 60 degrees, 90 degrees, and the like between each adjacent layer 26). 3D part 10 is further oriented such that the high tensile strains are also substantially parallel to the dominant road propagation direction of 3D part 10 at region 18. This can be particularly beneficial when the high tensile strains reach the elastic limits of the part material for printing the 3D part.

Figure 4:
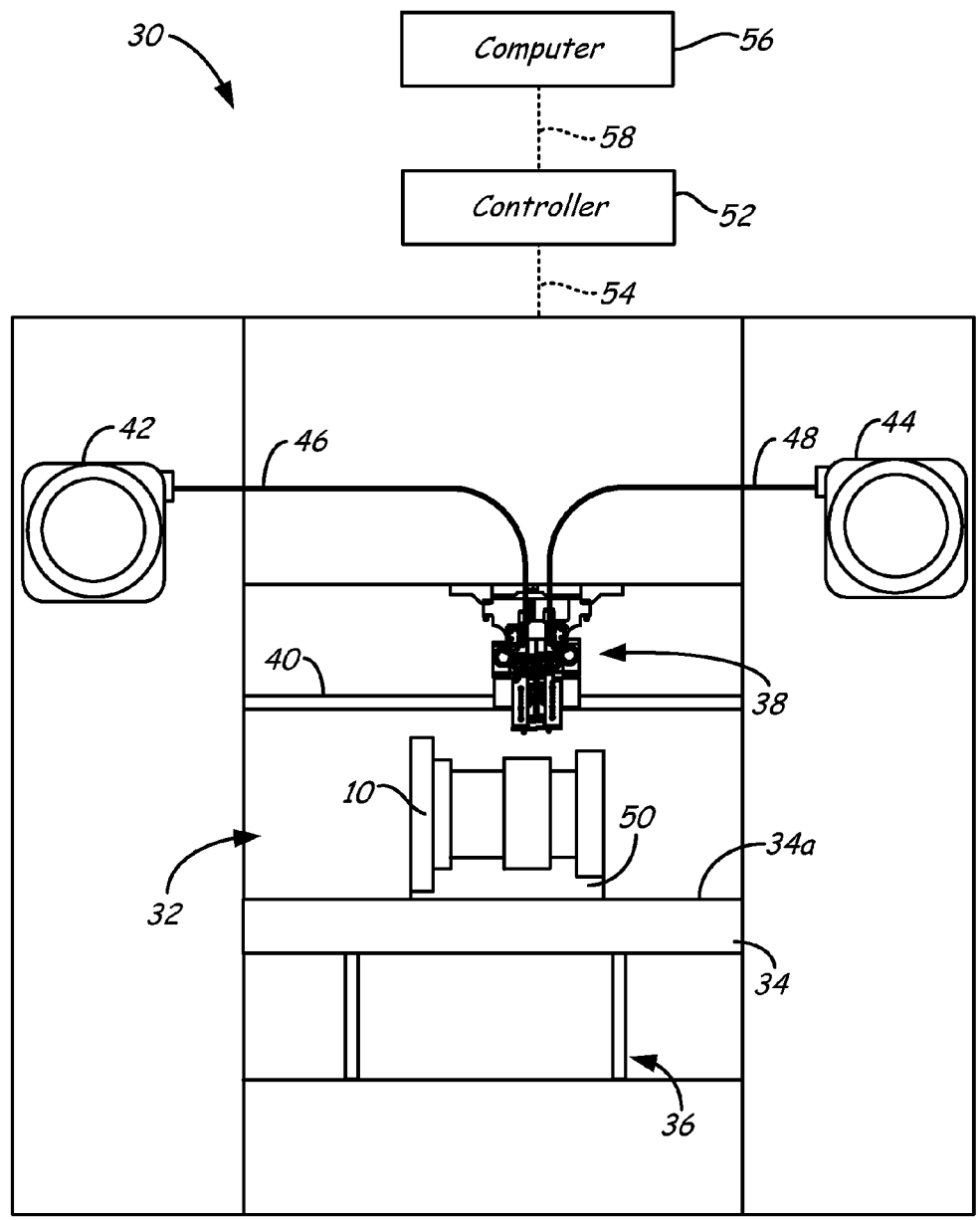
FIG. 4 is a front view of an additive manufacturing system configured to print 3D parts oriented pursuant to the method of the present disclosure.

Any suitable additive manufacturing system may be used to print the 3D part from the oriented digital model, such as extrusion-based systems, jetting systems, selective laser sintering systems, powder/binder jetting systems, electron-beam melting systems, and stereolithographic systems, and the like. FIG. 4 illustrates system 30, which is an example extrusion-based system for printing or otherwise building 3D parts (e.g., 3D part 10) using a layer-based, additive manufacturing technique from the oriented digital models. Suitable additive manufacturing systems for system 30 include extrusion-based additive manufacturing systems developed by Stratasys, Inc., Eden Prairie, Minn. under the trademark "FDM".

In the shown example, system 30 includes chamber 32, platen 34, platen gantry 36, print head 38, head gantry 40, and consumable assemblies 42 and 44. Chamber 32 is an enclosed environment that contains platen 34 for printing 3D parts and support structures. Chamber 32 may be heated (e.g., with circulating heated air) to reduce the rate at which the part and support materials solidify after being extruded and deposited (e.g., to reduce distortions and curling). In alternative embodiments, chamber 32 may be omitted and/or replaced with different types of build environments. For example, a 3D part and support structure may be printed in a build environment that is open to ambient conditions or may be enclosed with alternative structures (e.g., flexible curtains).

Platen 34 is a platform having platen surface 34a on which 3D parts (e.g., 3D part 10) and support structures are printed in a layer-by-layer manner, and is supported by platen gantry 36. In some embodiments, platen surface 34a may also include a removable substrate such as a flexible polymeric film or liner on which the 3D parts and support structures are printed, an adhesive tape, a painted-on layer of adhesive, a cardboard liner, or a build tray such as is disclosed in U.S. patent application Ser. No. 13/791,005.

Platen gantry 36 is a gantry assembly configured to move platen 34 along (or substantially along) the vertical z-axis. Correspondingly, print head 38 is supported by head gantry 40, which is a gantry assembly configured to move print head 38 in (or substantially in) the horizontal x-y build plane above chamber 32.

In the shown example, print head 38 is a dual-tip extrusion head configured to receive consumable filaments from consumable assemblies 42 and 44 (e.g., via guide tubes 46 and 48) for printing 3D part 10 and support structure 50 on platen surface 34a. Examples of suitable devices for print head 38, and the connections between print head 38 and head gantry 40 include those disclosed in Crump et al., U.S. Pat. No. 5,503,785; Swanson et al., U.S. Pat. No. 6,004,124; LaBossiere, et al., U.S. Pat. Nos. 7,384,255 and 7,604,470; Leavitt, U.S. Pat. No. 7,625,200; Batchelder et al., U.S. Pat. No. 7,896,209; and Comb et al., U.S. Pat. No. 8,153,182.

In additional embodiments, in which print head 38 is an interchangeable, single-nozzle print head, examples of suitable devices for each print head 38, and the connections between print head 38 and head gantry 40 include those disclosed in Swanson et al., U.S. Pat. No. 8,419,996. In jetting-based systems, print head 38 may be an inkjet head such as described in Kritchman et al., U.S. Pat. No. 8,323,017.

Consumable assembly 42 may contain a supply of a part material for printing 3D part 40. Correspondingly, consumable assembly 44 may contain a supply of a support material for printing support structure 50 from the given support material.

In an alternative embodiment, platen 34 may be configured to move in the horizontal x-y build plane within chamber 32, and print head 38 may be configured to move along the z-axis. Other similar arrangements may also be used such that one or both of platen 34 and print head 38 are moveable relative to each other. Platen 34 and print head 38 may also be oriented along different axes. For example, platen 34 may be oriented vertically and print head 38 may print 3D part 30 and support structure 32 along the x-axis or the y-axis.

System 30 also includes controller 52, which is one or more control circuits configured to monitor and operate the components of system 30. For example, one or more of the control functions performed by controller 52 can be implemented in hardware, software, firmware, and the like, or a combination thereof. Controller 52 may communicate over communication line 54 with chamber 32 (e.g., with a heating unit and/or air blower for chamber 32), platen gantry 36, print head 38, head gantry 40, and/or various sensors, calibration devices, display devices, and/or user input devices.

While illustrated as a single signal line, communication line 54 may include one or more electrical, optical, and/or wireless signal lines, allowing controller 52 to communicate with various components of system 30. Furthermore, while illustrated outside of system 30, controller 52 and communication line 54 may be internal components to system 30.

System 30 and/or controller 52 may also communicate with one or more computer-based systems, referred to as computer 56. Computer 56 may also be external and/or internal to system 30. For example, computer 56 may be one or more external computer systems (e.g., desktop, laptop, server-based, cloud-based, tablet, mobile media device, and the like) configured to communicate with system 30 and/or controller 52 over one or more wired and/or wireless communication lines, referred to as communication line 58.

Figure 5:
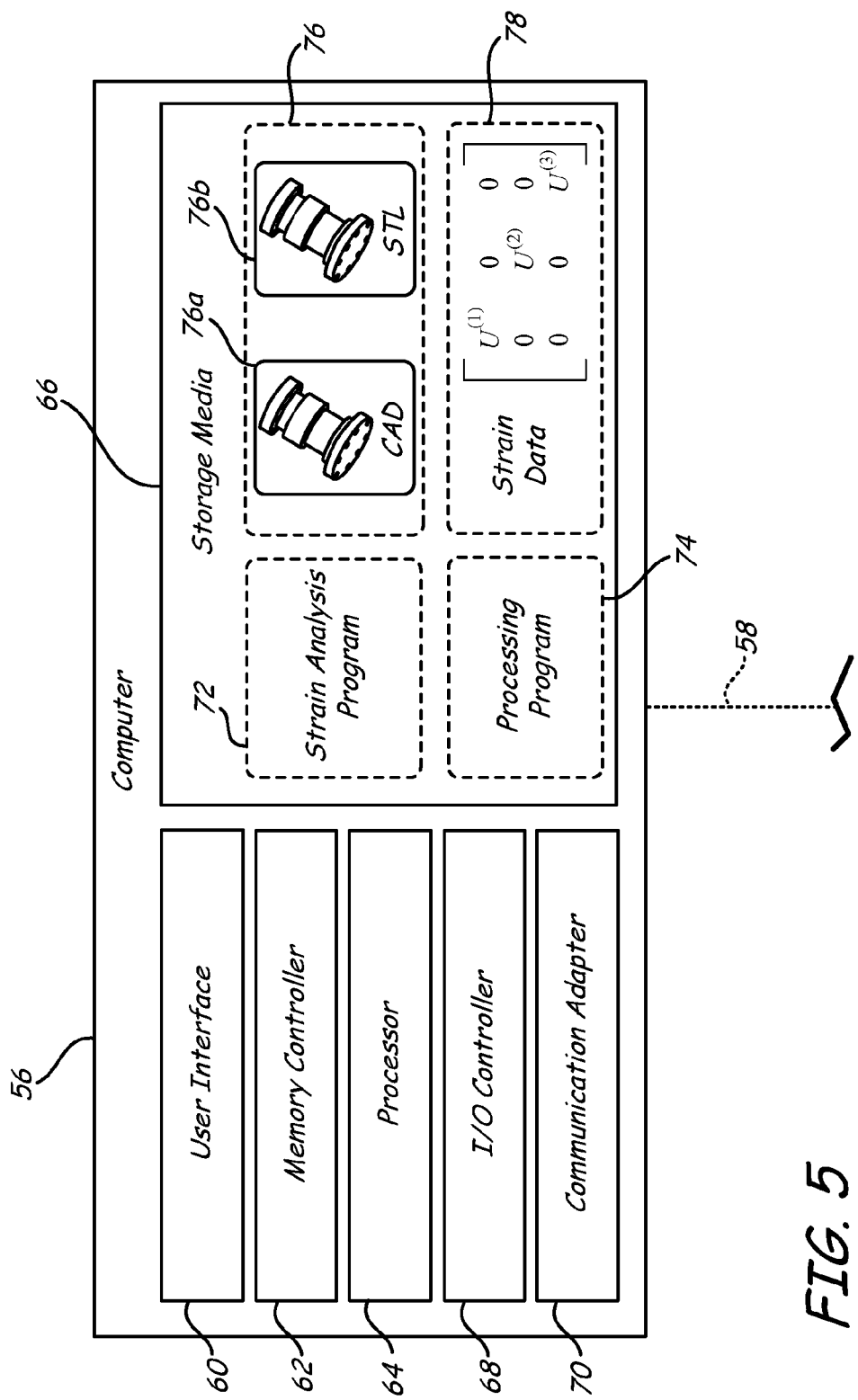
FIG. 5 is a schematic illustration of a computer for use with the additive manufacturing system.

As shown in FIG. 5, computer 56 may include any suitable computer-based hardware, such as user interface 60, memory controller 62, processor 64, storage media 66, input/output (I/O) controller 68, and communication adapter 70. Computer 56 may also include a variety of additional components that are contained in conventional computers, servers, and/or media devices.

User interface 60 is a user-operated interface (e.g., keyboards, touch pads, touch-screen displays, display monitors, and other eye, voice, movement, or hand-operated controls) configured to operate computer 56. Memory controller 62 is a circuit assembly that interfaces the components of computer 56 with one or more volatile random access memory (RAM) modules of storage media 66. Processor 64 is one or more computer-processing units configured to operate computer 56, and optionally, with memory controller 62, to perform the steps of the present method.

Storage media 66 is one or more internal and/or external data storage devices or computer storage media for computer 56, such as volatile RAM modules, read-only memory modules, optical media, magnetic media (e.g., hard disc drives), solid-state media (e.g., FLASH memory and solid-state drives), analog media, and the like. Storage media 66 may retain executable copies of strain analysis program 72 and processing program 74. Strain analysis program 72 may be any suitable programs for analyzing digital models to generate strain data (and stress and/or deformation data), such as an FEA program.

Processing program 74 may be any suitable pre-processing and/or post-processing program for orienting digital models, generating printing instructions from the oriented digital models (e.g., slicing the oriented digital models into layers, generating perimeter geometries and tool paths for each sliced layer, generating support structures and associated tool paths, print queuing, and the like), and transmitting the resulting printing instructions to system 30 and/or controller 52. Examples of suitable pre-processing programs includes those developed by Stratasys, Inc., Eden Prairie, Minn. under the trademarks "INSIGHT" and "CATALYST", which may be modified to orient digital models in the coordinate system based on the strain data from strain analysis program 72.

In some alternative embodiments, strain analysis program 72 may perform one or more functions of processing program 74, such as orienting the digital models based on the generated strain data. In further alternative embodiments, strain analysis program 72 and processing program 74 may be integrated into a single executable program or collection of programs that can be executed together.

Prior to a printing operation, computer 56 may receive one or more digital models of 3D parts to be printed with system 30. For instance, computer 56 may receive and store one or more digital models 76 on storage media 66, where digital model 76 can contain one or more digital model files of 3D part 10, such as a first digital model file 76a that may be analyzed by strain analysis program 72 (e.g., a CAD file) and a second digital model file 76b that may be processed with processing program 74 (e.g., an STL file).

Preferably, strain analysis program 72 and processing program 74 are configured to analyze and process the same digital model file (e.g., both can use the same STL file). However, some strain analysis programs are more effective at analyzing certain digital model files (e.g., CAD files) compared to other digital model files (e.g., STL files). In these situations, strain analysis program 72 may analyze digital model file 76a, and processing program may process digital model file 76b. For ease of reference, as used herein, the term "digital model" for a 3D part may refer to one or more digital model files for the 3D part, where the individual digital model files may have different file formats (e.g., CAD and STL file formats).

As discussed below, strain analysis program 72 is configured to analyze digital model 76 to produce strain data 78, where strain data 78 is one or more data files that may also be stored on storage media 66. Additionally, one or both of strain analysis program 72 and processing program 74 may generate and export one or more reports, which may be stored on storage media 66 and/or printed out. The reports may include a variety of information related to digital model 76, strain data 78 (e.g., FEA isostrain images), orientations of digital model 76, warning information, part material information, customer information, printing information, and the like. The reports may be retained with digital model 76 and strain data 78, and/or may be printed and shipped/stored with the printed 3D part 10.

I/O controller 68 is a circuit assembly that interfaces memory controller 62, processor 64, and storage media 66 with various input and output components of computer 56, including communication adapter 70. Communication adapter 70 is one or more wired or wireless transmitter/receiver adapters configured to communicate over communication line 58. For example, communication adapter 70 may include a serial port interface, universal serial bus (USB) interface, a FireWire interface, a parallel port interface, a direct local area network or internet connection adapter, a cellular wide area network transmitter/receiver, a Wi-Fi local area network transmitter/receiver, and/or combinations thereof.

In some embodiments, controller 52 itself may perform one or more of the operations typically performed by computer 56 or other components of system 30, such as generating printing instructions, performing compiler functions, and the like. Accordingly, controller 52 may also include the same computer-based hardware as computer 56. In further embodiments, controller 52 and computer 56 may be integrated into a common computer-based system or device that performs the operations of both controller 52 and computer 56.

Figure 6:
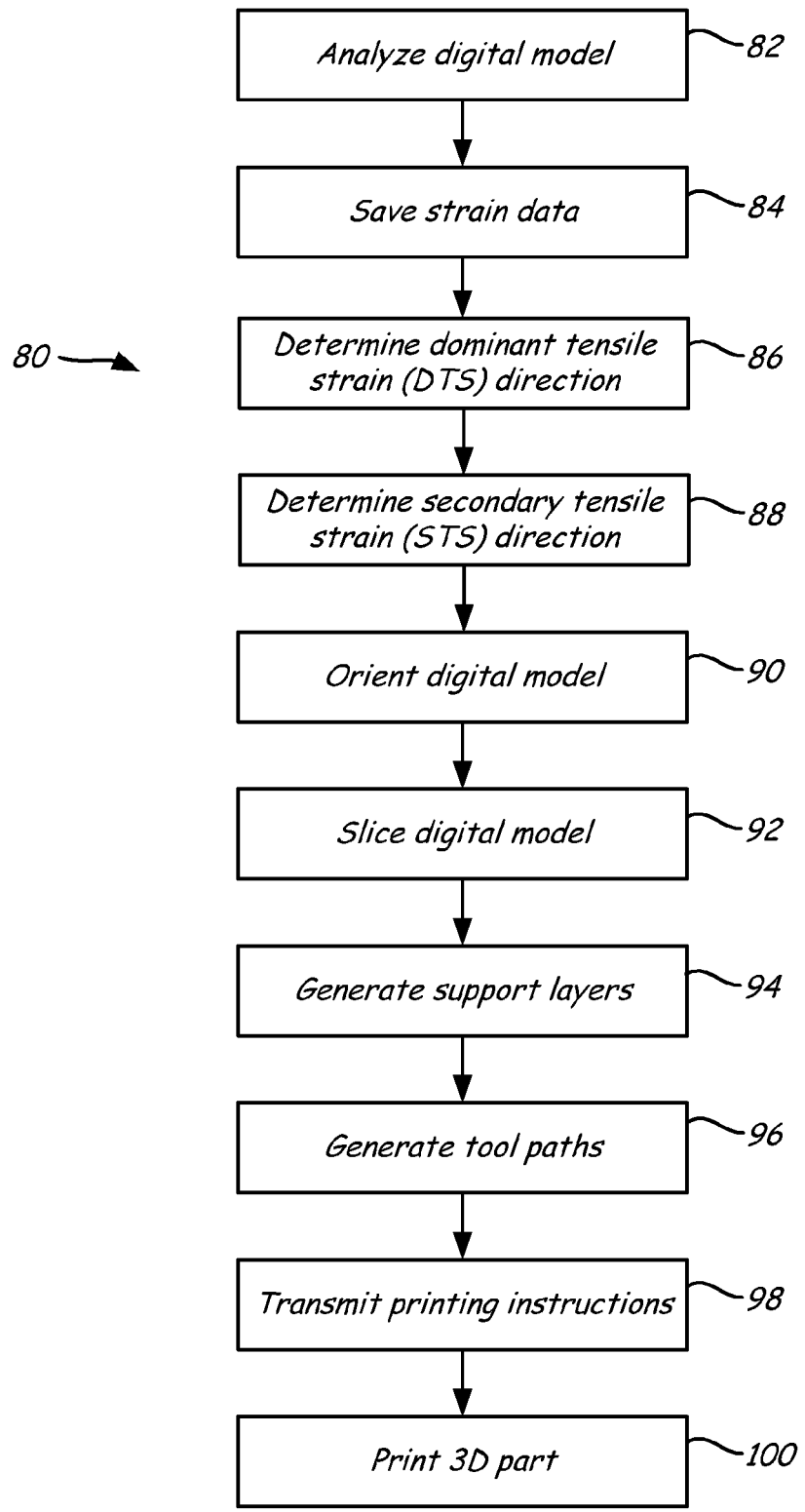
FIG. 6 is a flow diagram of the method of the present disclosure.

FIG. 6 is a flow diagram of method 80, which is an example method of the present disclosure for printing a 3D part (e.g., 3D part 10) with an orientation that aligns the directions of high strain in the build plane of the 3D part. As shown, method 80 includes steps 82-100, and initially involves analyzing digital model 76 with strain analysis program 62 (step 82). For example, a user may operate computer 56 via user interface 60 and execute strain analysis program 62 with computer 56 (e.g., with processor 64). Digital model 76 may then be loaded to the executed strain analysis program 62.

The user may also input the stress loads to be applied to 3D part 10 (e.g., the directions and magnitudes of these stress loads), material properties of 3D part 10, and the like into strain analysis program 62. This information may be loaded manually or from a previously-created file. Furthermore, strain analysis program 62 may also operate under one or more physical assumptions to simplify the calculations, such as assuming Hooke's law applies, that electrical fields are not being generated, that heat is not being dissipated, that digital model 76 represents a homogeneous solid part and/or has bulk properties of a given material (e.g., Young's modulus and Poisson's ratio), and the like.

Computer 56 may then use strain analysis program 62 to perform an analysis on digital model 76, such as a finite element analysis, to generate strain data 78. For example, computer 56 may generate a grid of voxels or nodes from digital model 76, preferably encompassing the volume of digital model 76. In alternative embodiments, digital model 76 may already contain data for the grid of voxels, such for use with voxel-based additive manufacturing techniques. In some embodiments, the number of voxels or nodes may be increased at the regions of expected higher strain to increase the data resolution in these regions.

Computer 56 may then generate strain tensors (and/or stress tensors) for at least a portion of the voxels or nodes of digital model 76. More preferably, computer 56 generates strain tensors (and/or stress tensors) for each voxel or node of digital model 76, encompassing the entire volume of digital model 76. Strain analysis program 72 preferably generates the strain tensor for each voxel as a diagonalized strain tensor, using the diagonal elements of the strain tensor to locally indicate the direction and magnitude of the tensile strains in digital model 76.

For example, if $\bar{x}$ is the at-rest position for each voxel of digital model 76, and $\bar{x}'$ is those same voxels upon being subjected to the stress load of arrow 16, the vector $\bar{u}$ describes the direction and magnitude of the motion of the voxels of digital model 76, as shown in Equation 1:

$$\bar{u} = \bar{x}' - \bar{x} \qquad \text{(Equation 1)}$$

More specifically, given two voxels or nodes in digital model 76 that are close together, the at-rest distance dl between the two voxels or nodes may be described by Equation 2:

$$dl = \sqrt{dx_1^2 + dx_2^2 + dx_3^2} \qquad \text{(Equation 2)}$$

and the distance dl' when 3D part 10 is subjected to a stress load (e.g., arrow 16) may be described by Equation 3:

$$dl' = \sqrt{dx'_1{}^2 + dx'_2{}^2 + dx'_3{}^2} \qquad \text{(Equation 3)}$$

Accordingly, the change between the at-rest distance dl and the distance dl' when subjected to the stress load may be described by Equation 4:

$$dl'^2 - dl^2 = \sum_{i=1}^{3} \sum_{k=1}^{3} 2u_{ik} dx_i dx_k \qquad \text{(Equation 4)}$$

where $u_{ik}$ is the strain tensor, which may be described in Cartesian coordinates by Equation 5:

$$u_{ik} = 0.5 \sum_{l=1}^{3} \left( \frac{\partial u_i}{\partial x_k} + \frac{\partial u_k}{\partial x_i} + \frac{\partial u_l}{\partial x_i} \frac{\partial u_l}{\partial x_k} \right) \qquad \text{(Equation 5)}$$

Because the third term in the strain tensor of Equation 5 is much smaller than the first two terms, the strain tensor of Equation 5 may be simplified to Equation 6:

$$u_{ik} = 0.5 \left( \frac{\partial u_i}{\partial x_k} + \frac{\partial u_k}{\partial x_i} \right) \qquad \text{(Equation 6)}$$

While there may be nine elements to the strain tensor, it is symmetric, so there are only six independent parameters. At any voxel or node in digital model 76, a coordinate rotation can be found where the off-diagonal elements of the strain tensor are zero. As such, for this coordinate system, the strain tensor is said to be diagonalized, and the diagonal values are the principal values of the strain tensor $u^{(1)}$, $u^{(2)}$, and $u^{(3)}$. The spatial distortion between the two test points for this diagonalized coordinate system may be described by $(1+u^{(1)})$ in the $\hat{x}_1$ direction, by $(1+u^{(2)})$ in the $\hat{x}_2$ direction, and by $(1+u^{(3)})$ in the $\hat{x}_3$ direction.

These diagonalized strain tensors may then be exported and saved as strain data 78, which may be stored on storage media 66 (step 84). Processing program 64 may then be executed with computer 56 (e.g., with processor 64) to process digital model 76 along with strain data 78. As explained below, this preferably involves determining a dominant tensile strain (DTS) direction and a secondary tensile strain (STS) direction from the strain data 78 (steps

86 and 88), and orienting digital model 76 such that the DTS direction and the STS direction are each aligned in the build plane (step 90).

For determining the DTS direction and the STS direction, computer 56 may effectively transform the diagonalized strain tensors back to the Cartesian coordinate system (or other coordinate system) used by system 30, such as by summing the positive values of each diagonalized strain tensor. Computer 56 may then vote over the volume V of digital model 76 (or at least the volume analyzed in step 82) to determine the volume-averaged tensile strain $u_i$ of digital model 76 in each $\vec{x}_i$ direction, which may be described by Equation 7:

$$U_i = \iiint_V d\left(\frac{dV \, U^{(i)}}{V}\right) V \qquad \text{(Equation 7)}$$

In order to differentiate tension from compression, computer 56 may operate under the assumption that the volume-averaged tensile strain $u_i$ is positive for tension and negative for compression. As such, computer 56 may set $u(x,y,z)=0$ if $u(x,y,z)<0$. Accordingly, for the $\hat{x}_1$ direction, the $\hat{x}_2$ direction, and the $\hat{x}_3$ direction, Equation 7 may be respectively described by Equations 8-10:

$$U_1 = \iiint_V d\left(\frac{dV \, U^{(1)}}{V}\right) V \qquad \text{(Equation 8)}$$

$$U_2 = \iiint_V d\left(\frac{dV \, U^{(2)}}{V}\right) V \qquad \text{(Equation 9)}$$

$$U_3 = \iiint_V d\left(\frac{dV \, U^{(3)}}{V}\right) V \qquad \text{(Equation 10)}$$

From Equations 8-10, computer 56 may then identify the volume-averaged tensile strain $u_i$ of digital model 76 having the greatest value, and assign the corresponding $\hat{x}_1$ direction as the DTS direction (step 86). Computer 56 may also identify the volume-averaged tensile strain $u_i$ of digital model 76 having the second or next greatest value, and assign the corresponding $\hat{x}_1$ direction as the STS direction (step 88). For example, if the volume-averaged tensile strain $u_1$ has the greatest value, and the volume-averaged tensile strain $u_2$ has the next greatest value (i.e., the volume-averaged tensile strain $u_3$ has the lowest value), computer 56 may assign the $\hat{x}_1$ direction as the DTS direction and assign the $\hat{x}_2$ direction as the STS direction.

In a preferred embodiment, computer 56 performs steps 86 and 88 by modifying the tensile strains with one or more weighted values, where the weighted value allows high tensile strains to have greater significance than low tensile strains. This is because the desired orientation of the printed 3D part 10 is highly dominated by the region of high tensile strain. For instance, Equation 7 may be modified to incorporate a power-based weighted value to calculate a weighted volume-averaged tensile strain $U_i^n$ as described by Equation 11:

$$U_i^n = \iiint_V d\left(\frac{dV \, (U^{(i)})^n}{V}\right) V \qquad \text{(Equation 11)}$$

where the weighted value n may be any suitable value, and is preferably greater than one (e.g., n=1.5, n=2, n=3, n=4, etc. . . . ) to provide greater significance to the voxels or nodes having high tensile strains, where the voxels or nodes having low tensile strains are effectively ignored.

As such, for the $\hat{x}_1$ direction, the $\hat{x}_2$ direction, and the $\hat{x}_3$ direction, Equation 11 may be respectively described by Equations 12-14:

$$U_1^n = \iiint_V d\left(\frac{dV \, (U^{(1)})^n}{V}\right) V \qquad \text{(Equation 12)}$$

$$U_2^n = \iiint_V d\left(\frac{dV \, (U^{(2)})^n}{V}\right) V \qquad \text{(Equation 13)}$$

$$U_3^n = \iiint_V d\left(\frac{dV \, (U^{(3)})^n}{V}\right) V \qquad \text{(Equation 14)}$$

Due to the ease of calculation, in a further embodiment, computer 56 may also calculate each of Equations 11-14 for multiple weighted values n, such as n=0, n=1, and n=2. For instance, computer 56 may calculate weighted volume-averaged tensile strains $U_1^0$ (i.e., n=0), $U_1^1$ (i.e., n=1), and $U_1^2$ (i.e., n=2). If they produce significantly different results from each other, and if the tensile strains in region 18 are substantially less than the elastic limit of the material for 3D part 10 (e.g., less than about 80% of the elastic limit), then the higher weighted value n (e.g., n=2) is preferably used for Equation 12. Computer 56 may perform the same calculations for weighted volume-averaged tensile strains $U_2^n$ and $U_3^n$. This further allows the computer 56 to select a weighted value n for each weighted volume-averaged tensile strain $U_1^n$, $U_2^n$, and $U_3^n$ in a manner that provides greater significance to the voxels or nodes having high tensile strains.

For Equations 12-14, computer 56 may then identify the weighted volume-averaged tensile strain $U_i^n$ of digital model 76 having the highest value, and assign the corresponding $\hat{x}_i$ direction as the DTS direction (step 86). Computer 56 may also identify the weighted volume-averaged tensile strain $U_i^n$ of digital model 76 having the next greatest value, and assign the corresponding $\hat{x}_i$ direction as the STS direction (step 88). This may be performed in the same manner as described above for Equations 8-10 in the non-weighted embodiment.

Computer 56 may then orient digital model 76 such that the DTS direction and the STS direction are each aligned in the build plane (step 90). This may involve pivoting or otherwise rotating digital model 76 from its initial position in the x-y-z coordinate system to an orientation in which the DTS direction and the STS direction each reside along any suitable axis in the x-y build plane.

As can be appreciated, if both the DTS direction and the STS direction already resides in the x-y build plane, then digital model 76 does not actually need to be pivoted or rotated in any direction. As such, as used herein, the terms "orient", "orienting", and the like do not necessarily require actual pivoting, rotation, or other movement of the digital model in the x-y-z coordinate system.

This orienting step aligns the directions of high tensile strain with the x-y build plane, as shown above in FIGS. 3A and 3B. As such, when digital model 76 is oriented in this manner, the resulting printed 3D part 10 that is printed by system 30 with the same orientation will have the high strains directed against the higher intralayer strength of 3D part 10. This effectively increases the strength of 3D part 10 for its intended use, and, for many applications, can vastly outweigh the longer build times and higher material consumptions. Furthermore, method 80 is suitable for efficiently orienting 3D parts having a variety of different strain profiles regardless of their complexities.

The orienting of digital model 76 in step 90 is preferably performed in a single orienting step. However, in alternative embodiments, multiple successive orienting steps may be used. For example, computer 56 may initially orient digital model 76 to align the DTS direction in the x-y build plane, and then rotate digital model 76 around an axis of the DTS direction to also align the STS direction in the x-y build plane, or vice versa.

In some embodiments, computer 56 may further orient digital model 76 to account for secondary purposes, such as reduced build time, reduced material consumption, part packing, and the like, so long as the DTS direction and the STS direction each remain aligned or substantially aligned in the x-y build plane. For instance, the DTS direction may be aligned with the dominant road propagation direction of 3D part 10 at region 18, and the STS direction may be oriented perpendicular to the dominant road propagation direction, while still residing in the x-y build plane.

After digital model 76 is properly oriented, computer 56 may then also operate processing program 74 to generate printing instructions, such as slicing the oriented digital model 76 into layers (step 92), generating tool paths for support structure 50 associated with the sliced layers of the oriented digital model 76 (step 94), and generating tool paths for the sliced layers of the oriented digital model 76 (step 96). As discussed below, in some preferred embodiments, computer 56 may also utilize processing program 74 to optimize the tool path fill pattern for one or more of the sliced layers of the oriented digital model 76 (more preferably, for each sliced layer) based on strain data 78. Computer 56 may then transmit the resulting printing instructions to system 30 and/or controller 52 to print 3D part 10 based on the oriented digital model 76 (step 98).

During the printing operation (step 100), controller 52 may direct platen gantry 36 to move platen 34 to a predetermined height within chamber 32. Controller 52 may then direct head gantry 40 to move print head 38 around in the horizontal x-y plane above chamber 32. Controller 52 may also direct print head 38 to selectively draw successive segments of the consumable filaments from container portions 42 and 44, and through guide tubes 46 and 48, respectively. This thermally melts the received successive segments such that the consumable filaments become molten materials.

The molten materials are then selectively extruded from print head 38 and deposited onto platen 34 for printing 3D part 10 and support structure 50, in a layer-by-layer manner, based on the received printing instructions. The printed 3D part 10 is oriented in the x-y-z coordinate system such that the intended directions of the high tensile strains are aligned in the x-y build plane (as shown in FIGS. 3A and 3B). This correspondingly directs the high strain primarily against the higher intralayer strength of 3D part 10, compared to the relatively lower interlayer strength of 3D part 10.

Suitable consumable materials for 3D part 10 and support structure 50 include those disclosed and listed in Crump et al., U.S. Pat. No. 5,503,785; Lombardi et al., U.S. Pat. Nos. 6,070,107 and 6,228,923; Priedeman et al., U.S. Pat. No. 6,790,403; Comb et al., U.S. Pat. No. 7,122,246; Batchelder, U.S. Patent Application Publication No. 2009/0263582; Hopkins et al., U.S. Patent Application Publication No. 2010/0096072; Batchelder et al., U.S. Patent Application Publication No. 2011/0076496; and Batchelder et al., U.S. Patent Application Publication No. 2011/0076495.

After the printing operation is completed, the resulting printed 3D part 10 and support structure 50 may be removed from system 30, and 3D part 10 may be removed from support structure 50. For example, the printed 3D part 10 and support structure 50 may be placed in an aqueous liquid or solution to dissolve the soluble support material of support structure 50. The resulting 3D part 10 may then be removed from the aqueous liquid or solution for subsequent post-processing, if desired.

Figure 7:
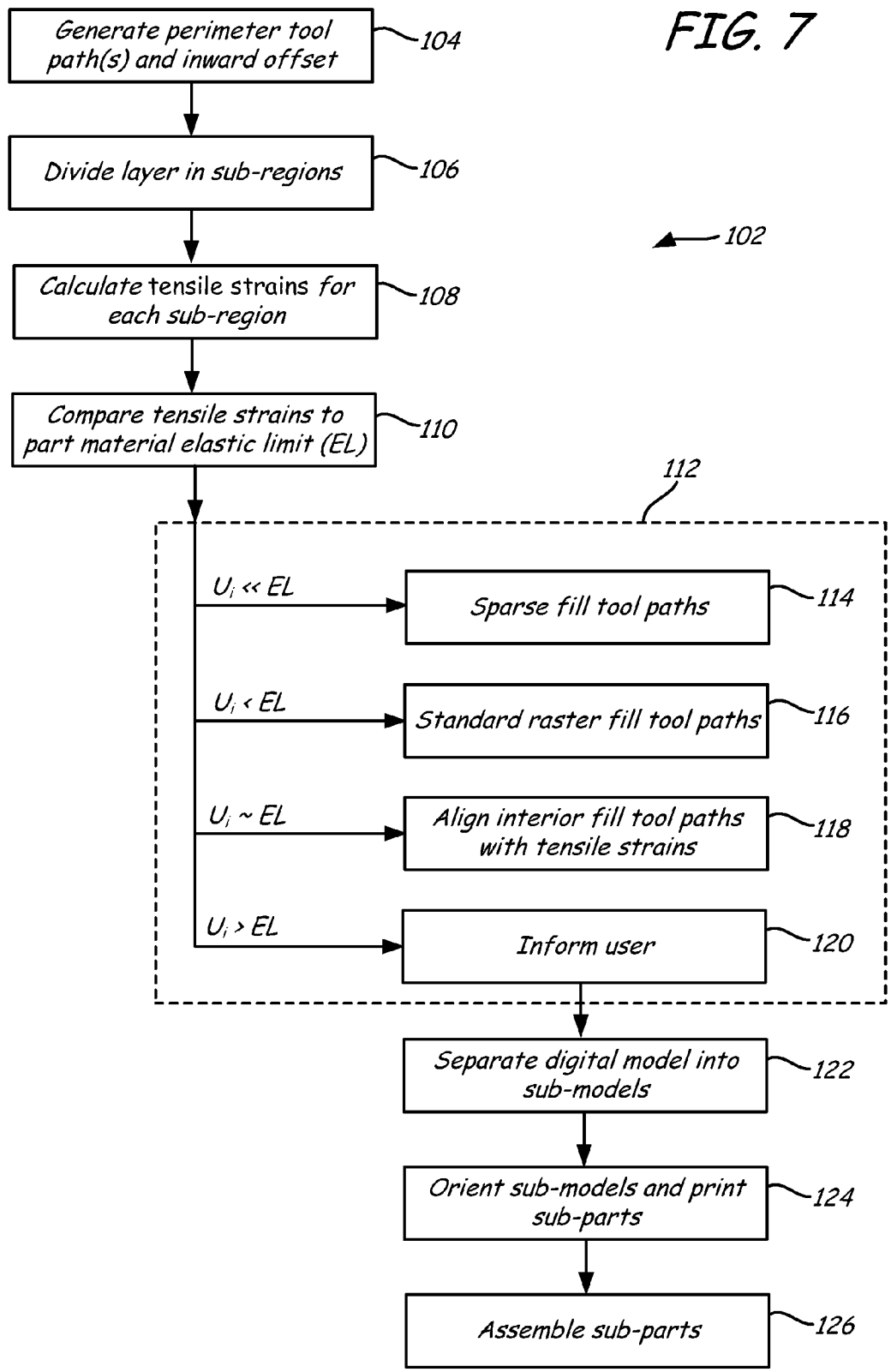
FIG. 7 is a flow diagram of a method for generating interior fill tool paths, pursuant to an embodiment of the method of the present disclosure.

As mentioned above, the interior fill tool paths of each sliced layer may also be generated based on strain data 78. FIG. 7 is a flow diagram of method 102, which may be performed on each sliced layer of digital model 76 by computer 56. As shown, method 102 includes steps 104-126, and initially involves generating one or more perimeter tool paths for a given sliced layer, and optionally, designating an inward offset distance to define an interior region for the sliced layer (step 104).

Computer 56 may then divide the sliced layer into multiple sub-regions (step 106). This may be performed in a variety of manners, such as by dividing the layer into preset areas. Then, for each sub-region, computer 56 may calculate the local volume-averaged tensile strains $u_1$, $u_2$, and $u_3$, such as by Equations 8-10 (or alternatively by Equations 12-14), where the volume V is based on the area of the sub-region and the slice thickness (step 108).

Computer 56 may then compare the local volume-averaged tensile strains $u_1$, $u_2$, $u_3$, to the elastic limit (EL) of the part material used to print 3D part 10 (step 110). For example, computer 56 may compare the highest and second highest local volume-averaged tensile strains (e.g., $u_1$ and $u_2$) and/or their Pythagorean sum to the elastic limit of the part material, and generate the interior fill tool path(s) for the sub-region based on the comparison (step 112).

Step 112 may include one or more different tool-path patterns based on the comparison in step 110, such as those illustrated in steps 114-120. For instance, if the local volume-averaged tensile strains $u_1$ and $u_2$, and/or their Pythagorean sum, are substantially less than the elastic limit of the part material (e.g., less than about 10% of the elastic limit), then computer 56 may generate the interior fill tool path for that sub-region with a sparse-fill pattern (step 114). This can achieved because the given sub-region is not expected to be subjected to any substantial stress loads, and can be beneficial for reducing printing times, part material consumption, and part weight, if desired.

Alternatively, if the local volume-averaged tensile strains $u_1$ and $u_2$, and/or their Pythagorean sum, are less than the elastic limit of the part material (e.g., from about 10% to less than about 80% of the elastic limit), then computer 56 may generate the interior fill tool path for that sub-region with a standard raster-fill pattern (step 116).

Furthermore, if the local volume-averaged tensile strains $u_1$ and $u_2$, and/or their Pythagorean sum, are similar to or slightly less than the elastic limit of the part material (e.g., from about 80% to about 100% of the elastic limit), then computer 56 may generate the interior fill tool path for that sub-region in a manner that aligns the tool paths with the direction of the greatest tensile strain (step 118). This may be performed in the same manner as for determining the DTS direction and/or the STS direction for the given sub-region of the sliced layer.

In particular, computer 56 may generate a raster-fill pattern where the primary tool paths of the raster-fill pattern may be aligned with the $\hat{x}_1$ direction, and optionally, secondary tool paths of the raster-fill pattern may be aligned with the $\hat{x}_2$ direction. Aligning the primary tool paths of the raster-fill pattern may be aligned with the $\hat{x}_1$ direction directs the local high tensile strains in the sub-region primarily against the deposited roads of the part material (that are deposited along the tool paths), as opposed to directing the local high tensile strains against the weaker bonds between the deposited roads.

Finally, if the local volume-averaged tensile strains $u_1$ and $u_2$, and/or their Pythagorean sum, are greater than the elastic limit of the part material, then computer 56 may generate a warning notice to inform the user of this with user interface 60 (step 120). The user may then decide how to proceed based on this information. Computer 56 may also display recommendations with user interface 60 on how the user should proceed, such as recommending a higher-strength material to print 3D part 10.

In one embodiment, computer 56 may separate digital model 76 into two or more sub-models, preferably at locations of low compressive and tensile strains (step 122). Alternatively, the user may manually perform this action with computer 56 (or another computer-based system). Computer 56 may also display recommendations with user interface 60 on how the user should proceed, such as recommending higher-strength materials for the sub-models located at the high strain regions. This accordingly allows higher strength and more expensive materials to be used at regions of high tensile strains, and lower strength and less expensive materials to be used at regions of lower tensile strains.

If digital model 76 is separated into two or more sub-models, computer 56 and system 30 may perform the steps of method 80 to orient each sub-model in the same manner as discussed above for digital model 76. Computer 56 may then generate printing instructions based on each oriented sub-part, and transmit the generated printing instructions to system 30. System 30 may then use the received printing instructions for each oriented sub-model to print a sub-part, where the sub-parts may be printed from different materials (e.g., different strength materials) (step 124). After the sub-parts are printed, they may be assembled together to produce 3D part 10 using any suitable technique, such as radiation (e.g., microwave) welding, solvent welding, thermal welding, mechanical interlocking, and combinations thereof (step 126).

For example, if computer 56 identifies that region 18 of 3D part 10 will be subjected to tensile strains that exceed the elastic limit of the originally-intended part material, computer 56 may separate digital model 76 into a first sub-model (having region 18 of 3D part 10), and a second sub-model (encompassing the remainder of 3D part 10), where the first and second sub-models are preferably separated at a location of low strain. Computer 56 may then independently perform method 80 (and optionally method 102) on each sub-model to orient each sub-model, generate printing instructions for each sub-model, and transmit the printing instructions for each sub-model to system 30.

System 30 may then print a first sub-part from the printing instructions of the first oriented sub-model, preferably from a higher-strength part material that has an elastic limit greater than the expected tensile strains at region 18. System 30 may also print a second sub-part from the printing instructions of the second oriented sub-model, which may be printed from the originally-intended, lower-strength part material. The first and second sub-parts may be printed in the same build run, or in separate build runs. After being printed optionally undergoing one or more post-build operations (e.g., support removal), the first and second sub-parts may be assembled together to produce 3D part 10 having the higher-strength part material at region 18.

Computer 56 may also separate digital model 76 into two or more sub-models to accommodate multiple high stress loads at different regions and directions along 3D part 10. If computer 56 identifies that 3D part 10 will be subjected to multiple high stress loads that are separated by lower-strain regions of 3D part 10, computer 56 may separate digital model 76 into sub-models at these lower lower-strain regions, and then orient and print each sub-model in the same manner as discussed above. This is beneficial for effectively increasing the part strength of the assembled 3D part 10 even when subjected to stress loads at different locations and directions along 3D part 10.

Although the present disclosure has been described with reference to preferred embodiments, workers skilled in the art will recognize that changes may be made in form and detail without departing from the spirit and scope of the disclosure.

The invention claimed is:

1. A method for printing a three-dimensional part with an additive manufacturing system, the method comprising:
providing a digital model of the three-dimensional part to a computer-based system;
generating strain data from the digital model with the computer-based system, wherein generating the strain data comprises generating strain tensors for a plurality of voxels of the digital model;
determining a dominant tensile strain direction for the digital model from the strain data with the computer-based system;
orienting the digital model to align the dominant tensile strain direction in a build plane of the additive manufacturing system; and
generating printing instructions from the oriented digital model with the computer-based system.

2. The method of claim 1, wherein the method further comprises saving one or more files of the generated strain tensors to one or more storage media of the computer-based system.

3. The method of claim 1, wherein the generated strain tensors for the digital model comprise diagonalized strain tensors.

4. The method of claim 1, and further comprising:
slicing the oriented digital model into a plurality of sliced layers with the computer-based system, wherein the plurality of sliced layers comprise a first sliced layer;
separating the first sliced layer into a plurality of sub-regions with the computer-based system, wherein the plurality of sub-regions comprise a first sub-region;
calculating volume-averaged tensile strains for the first sub-region from the strain data with the computer-based system;
comparing, with the computer-based system, at least one of the calculated volume-averaged tensile strains to an elastic limit for a part material used to print the three-dimensional part; and
generating one or more interior fill tool paths for the first sub-region based on the comparison with the computer-based system.

5. The method of claim 1, and further comprising determining a secondary tensile strain direction for the digital model from the strain data with the computer-based system, wherein orienting the digital model also aligns the secondary tensile strain direction in the build plane of the additive manufacturing system.

6. The method of claim 5, and further comprising calculating volume-averaged tensile strains from the strain data with the computer-based system, wherein the calculated volume-averaged tensile strains comprise a highest volume-averaged tensile strain and a second highest volume-averaged tensile strain, wherein determining the dominant tensile strain direction from the strain data comprises assigning a first coordinate direction for the highest volume-averaged tensile strain as the dominant tensile strain direction, and wherein determining the secondary tensile strain direction from the strain data comprises assigning a second coordinate direction for the second highest volume-averaged tensile strain as the secondary tensile strain direction.

7. The method of claim 6, wherein calculating the volume-averaged tensile strains from the strain data comprises calculating weighted volume-averaged tensile strains from the strain data and from one or more weighted values.

8. The method of claim 1, and further comprising:
transmitting the generated printing instructions from the computer-based system to the additive manufacturing system; and
printing the three-dimensional part in a layer-by-layer manner based on the transmitted printing instructions.

9. The method of claim 1, and further comprising:
separating the digital model into sub-models based on the generated strain data with the computer-based system, wherein orienting the digital model comprises orienting a first sub-model of the sub-models, and wherein generating the printing instructions from the oriented digital model comprises generating the printing instructions from the oriented first sub-model; and
printing a first sub-part in a layer-by-layer manner based on the generated printing instructions.

10. The method of claim 9, wherein the first-sub part is printed from a first part material, and wherein the method further comprises:
orienting a second sub-model of the sub-models with the computer-based system;
printing a second sub-part of the three-dimensional part in the layer-by-layer manner based on the oriented second sub-model, wherein the second sub-part is printed from a second part material that is different from the first part material; and
assembling the first sub-part and the second sub-part together produce at least a portion of the three-dimensional part.

11. A method for printing a three-dimensional part with an additive manufacturing system, the method comprising:
performing a finite element analysis on a digital model with a computer-based system to produce a plurality of strain tensors each associated with a voxel of the digital model;
calculating volume-averaged tensile strains from the plurality of strain tensors with the computer-based system;
determining a dominant tensile strain direction for the digital model from the calculated volume-averaged tensile strains with the computer-based system;
determining a secondary tensile strain direction for the digital model from the calculated volume-averaged tensile strains with the computer-based system;
orienting, with the computer-based system, the digital model to align each of the dominant tensile strain direction and the secondary tensile strain direction in a build plane of the additive manufacturing system;
generating printing instructions based on the oriented digital model with the computer-based system; and
printing the three-dimensional part in a layer-by-layer manner with the additive manufacturing system based on the generated printing instructions.

12. The method of claim 11, wherein calculating the volume-averaged tensile strains from the plurality of strain tensors comprises calculating weighted volume-averaged tensile strains from the plurality of strain tensors and from one or more weighted values.

13. The method of claim 11, wherein the strain tensors comprise diagonalized strain tensors.

14. The method of claim 11, wherein generating the printing instructions comprises:
slicing the oriented digital model into a plurality of sliced layers with the computer-based system, wherein the plurality of sliced layers comprise a first sliced layer;
separating the first sliced layer into a plurality of sub-regions with the computer-based system, wherein the plurality of sub-regions comprise a first sub-region;
calculating, with the computer-based system, local volume-averaged tensile strains for the first sub-region from the strain tensors associated with the first sub-region;
comparing, with the computer-based system, at least one of the calculated local volume-averaged tensile strains for the first sub-region to an elastic limit for a part material used to print the three-dimensional part; and
generating one or more interior fill tool paths for the first sub-region based on the comparison with the computer-based system.

15. The method of claim 14, wherein the calculated local volume-averaged tensile strains for the first sub-region comprise a highest local volume-averaged tensile strain, and wherein generating the interior fill tool path for the first sub-region comprises aligning at least a portion of the interior fill tool paths with a coordinate direction for the highest local volume-averaged tensile strain.

16. A program stored on a computer storage medium, and configured to be operated by a processor of a computer-based system to perform steps that comprise:
generating strain data for a digital model, wherein generating the strain data comprises generating strain tensors for a plurality of nodes of the digital model;
determining a dominant tensile strain direction for the digital model from the generated strain data as a function of the strain tensors;
orienting the digital model to align the dominant tensile strain direction in a build plane of an additive manufacturing system associated with the program;
generating printing instructions based on the oriented digital model; and
transmitting the generated printing instructions from the computer-based system to the associated additive manufacturing system for printing a three-dimensional part in a layer-by-layer manner with the additive manufacturing system based on the generated printing instructions.

17. The program of claim 16, wherein the performed steps further comprise saving one or more files of the generated strain tensors to one or more storage media of the computer-based system.

18. The method of claim 16, wherein the performed steps further comprise determining a secondary tensile strain direction for the digital model from the strain data with the computer-based system, wherein the performed step of orienting the digital model also aligns the secondary tensile strain direction in the build plane of the additive manufacturing system.

19. The program of claim 18, wherein the performed steps further comprise calculating volume-averaged tensile strains from the strain data, wherein the calculated volume-averaged tensile strains comprise a highest volume-averaged tensile strain and a second highest volume-averaged tensile strain, wherein the performed step of determining the dominant tensile strain direction from the strain data comprises assigning a first coordinate direction for the highest volume-averaged tensile strain as the dominant tensile strain direction, and wherein the performed step of determining the secondary tensile strain direction from the strain data comprises assigning a second coordinate direction for the second highest volume-averaged tensile strain as the secondary tensile strain direction.

20. The program of claim 16, wherein the performed step of generating the printing instructions comprises:
   slicing the oriented digital model into a plurality of sliced layers, wherein the plurality of sliced layers comprise a first sliced layer;
   separating the first sliced layer into a plurality of sub-regions, wherein the plurality of sub-regions comprise a first sub-region;
   calculating local volume-averaged tensile strains for the first sub-region from the strain tensors associated with the first sub-region;
   comparing at least one of the calculated local volume-averaged tensile strains for the first sub-region to an elastic limit for a part material used to print the three-dimensional part; and
   generating one or more interior fill tool paths for the first sub-region based on the comparison.

* * * * *